(12) United States Patent
DiMaggio

(10) Patent No.: US 7,090,179 B2
(45) Date of Patent: Aug. 15, 2006

(54) MOUNTING ASSEMBLY FOR A WASTE LINE OF A MEDICAL TREATMENT APPARATUS

(76) Inventor: Edward G. DiMaggio, 45110 Sub Station Rd., Hammond, LA (US) 70401

( * ) Notice: Subject to any disclaimer, the term of this patent is extended or adjusted under 35 U.S.C. 154(b) by 126 days.

(21) Appl. No.: 10/969,168

(22) Filed: Oct. 20, 2004

(65) Prior Publication Data

US 2005/0161563 A1 Jul. 28, 2005

Related U.S. Application Data

(63) Continuation-in-part of application No. 10/764,230, filed on Jan. 23, 2004, now Pat. No. 6,926,239.

(51) Int. Cl.
*F16B 47/00* (2006.01)

(52) U.S. Cl. .................. 248/206.1; 75/206.2; 75/302; 75/505

(58) Field of Classification Search ............. 248/206.2, 248/75, 76, 80, 505, 500, 206.1, 205.7, 205.5, 248/205.6, 363, 303, 304, 362, 302
See application file for complete search history.

(56) References Cited

U.S. PATENT DOCUMENTS

| | | | |
|---|---|---|---|
| RE21,391 E | * | 3/1940 | Holden .................. 248/75 |
| 3,685,680 A | | 8/1972 | Tenckhoff et al. |
| 5,491,870 A | * | 2/1996 | Holmes .................. 15/301 |
| 6,234,992 B1 | | 5/2001 | Haight et al. |
| 6,237,654 B1 | | 5/2001 | Sheyer |
| 6,280,634 B1 | | 8/2001 | Shah et al. |
| 6,348,162 B1 | | 2/2002 | Ash |
| 6,588,803 B1 | | 7/2003 | Vila |
| 6,632,189 B1 | | 10/2003 | Fallen et al. |
| 2002/0023879 A1 | | 2/2002 | Hadden |
| 2002/0077608 A1 | | 6/2002 | Stringer et al. |
| 2002/0123715 A1 | | 9/2002 | Sorenson et al. |
| 2002/0171022 A1 | * | 11/2002 | Hsu ......................... 248/505 |
| 2002/0174483 A1 | | 11/2002 | Gallant |
| 2003/0043688 A1 | | 3/2003 | Peterson et al. |
| 2003/0163078 A1 | | 8/2003 | Fallen et al. |
| 2004/0211875 A1 | * | 10/2004 | Wisniewski et al. ........ 248/500 |
| 2005/0193487 A1 | * | 9/2005 | Watari .......................... 4/570 |

* cited by examiner

*Primary Examiner*—Ramon O Ramirez
(74) *Attorney, Agent, or Firm*—Keaty Professional Law Corporation

(57) ABSTRACT

A mounting assembly for a discharge conduit of a medical treatment device, such as a dialysis machine. The mounting assembly has a connector member detachably engageable with a discharge nozzle of a discharge conduit and a suction cup that can be mounted on a rim of a waste receptor, such as a sink or a toilet bow. To ensure proper orientation of the discharge outlet above an opening of a waste receptor, the mounting assembly provides for a rigid securing clamp that engages the discharge nozzle and hooks to a rim, or under a rim of the waste receptor. The mounting assembly supports the discharge nozzle directly above the opening of the waste receptor, thereby facilitating discharge of the liquid waste directly into a municipal sewage line.

18 Claims, 3 Drawing Sheets

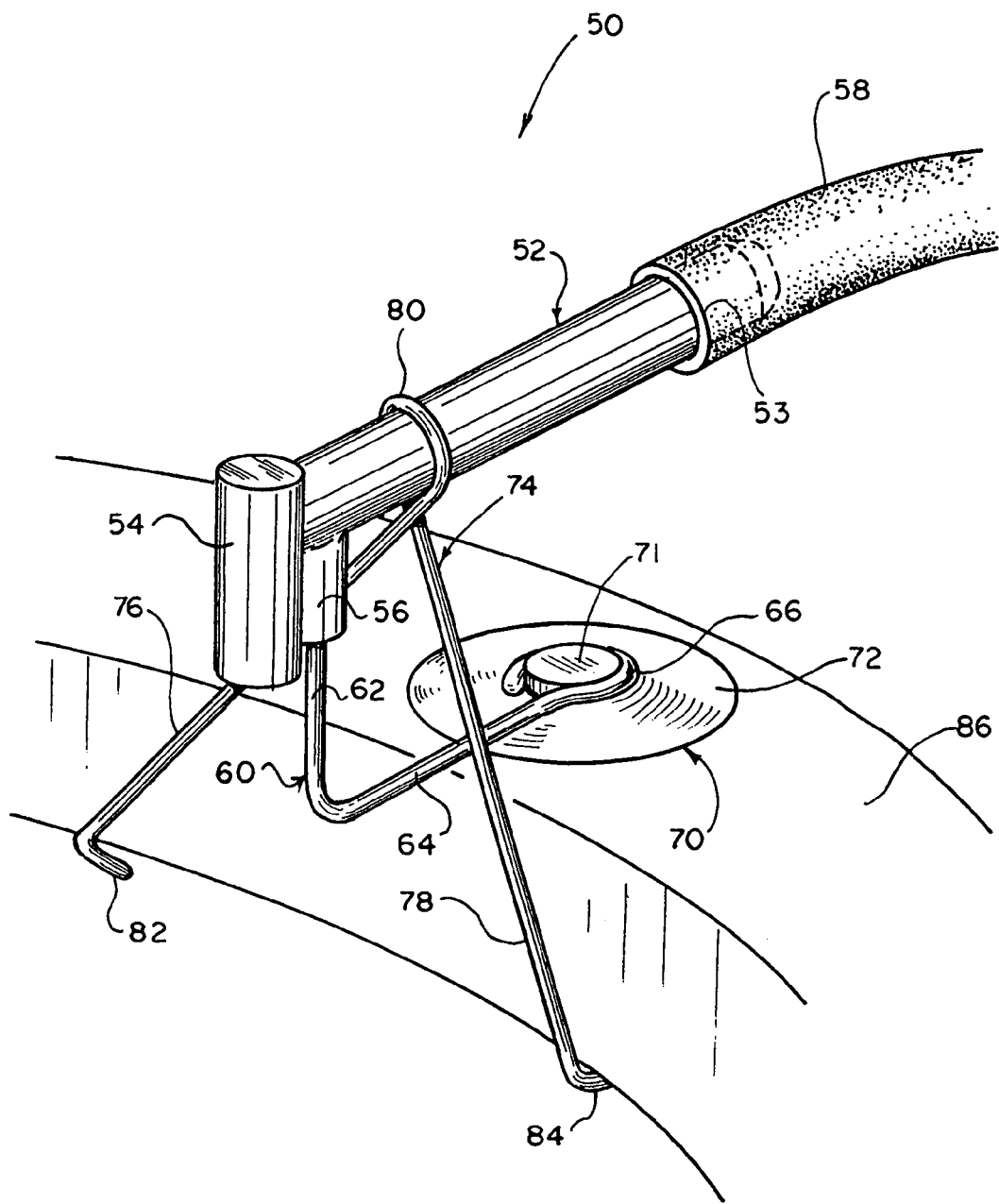
F I G. 3

MOUNTING ASSEMBLY FOR A WASTE LINE OF A MEDICAL TREATMENT APPARATUS

CROSS-REFERENCE TO RELATED APPLICATIONS

This application is a continuation-in-part of my application Ser. No. 10/764,230 filed on Jan. 23, 2004 now U.S. Pat. No. 6,926,239 for "Mounting Assembly for a Waste Discharge Line of a Medical Treatment Apparatus," the full disclosure of which is incorporated by reference herein.

BACKGROUND OF THE INVENTION

This invention relates to an accessory for a medical treatment apparatus, such as for instance, a dialysis machine, and more particularly to a support assembly for a drainage tube that is used to promote the drainage of fluids from a waste side of a dialysis machine in an efficient and sanitary manner.

The kidneys perform one of the most important functions in the elimination of waste in a human body; they filter out extra water and waste, thereby cleaning the blood and facilitating production of an adequate level of red blood cells. When the kidneys fail, the fluids are retained in the blood and do not circulate in the proper fashion through the body. As a consequence, waste material builds up in the body seriously endangering health and wellbeing of the person.

Dialysis imitates the work of a kidney. Technology has developed two types of dialysis treatment: hemodialysis and peritoneal dialysis. The majority of the patients receive hemodialysis, by which the blood is circulated outside the body and cleaned inside the machine before returning to the patient. The patent's blood is drained into the dialysis machine and a fluid called dialysate is also circulated through the machine. A thin, semi-permeable membrane separates the part that circulates the blood and the second part for the dialysate. As dialysate processes on one side of the membrane, and blood on the other, particles in waste from the blood stream pass through the microscopic holes formed in the membrane and are washed away in the dialysate. Blood cells being too large to go through the membrane holes are returned to the body.

The other type of treatment, peritoneal dialysis, uses the patient's own peritoneal membrane as a filter. The peritoneal membrane is a sack around the abdominal organs. This membrane is semi-permeable allowing waste particles to go through it but preventing larger blood cells to penetrate the membrane. In this type of treatment, a patient has a plastic tube catheter surgically implanted into the abdominal wall. The patient's caregiver slowly empties the dialysate fluid into the catheter and exposes the blood to the dialysate through the peritoneal membrane. Similarly to the hemodialysis method, the waste particles are removed with the dialysate and are discarded.

The peritoneal dialysis method has distinct advantages as it allows to significantly reduce the time needed for the dialysate to clean the blood and remove the waste. Additionally, the patient can perform the procedure in a non-hospital setting or at thousands of locations around the world. Such type of treatment may be administered by a caregiver that may not be very experienced in other types of the dialysis procedure.

When the patient or a caregiver performs the dialysis treatment, the waste is drained into a bag or other container, which can then be emptied into a waste receptor, such as a sink or a toilet. Needless to say, the bag is quite heavy and cumbersome to handle. Various solutions have been offered to assist in disposing of the waste drained from a medical treatment device. For instance, U.S. Pat. No. 5,503,633 issued on Apr. 2, 1996 for "Ostomy Bag Cleaning Apparatus" discloses a device, which allows a patient to drain the waste from the ostomy bag into a toilet without disengaging the bag from the patient's body. The device uses a support for a patient at a sufficient height above a toilet bowl in the form of a platform with support bars that are mounted on the toilet. A hose attached to a house water supply allows cleaning of the ostomy bag while the patient is seated on the platform.

Another solution is offered in U.S. patent application No. 2002/0077608 published on Jun. 20, 2002 and entitled "Peritoneal Waste Bag Support and Drainage Device". The application discloses a collapsible table, which supports a peritoneal waste bag in a desired location, for instance, adjacent a toilet. A waste bag is placed on top of the table, with a plug of the waste bag being oriented above the toilet bowl. The height of the legs is adjusted to allow the table to be tilted and facilitate drainage of the waste bag content by gravity directly into the toilet.

Municipal and state plumbing codes allow drainage of dialysis waste directly into the municipal waste channels. However, the municipal and state codes also require that the drainage from a fixture, device or appliance that discharges directly into a sink or other waste receptor terminate at a point below the flood level end of the sink. The same codes also require that an unobstructed horizontal distance of be formed between the outside of the indirect waste pipe and the inside of the receiving sink or toilet so as to allow a backflow of sewerage to spill over the flood level rim of the receiving sink or receptacle and thereby prevent the backflow from reaching the fixture, device, or appliance which is served by the indirect waste pipe.

Another provision of the plumbing code requires that the check valve be installed in the drain or in the sewer or drainage system to prevent sewerage or drainage from backing into lower levels through the fixtures or devices not installed sufficiently above floor or drainage systems. Therefore, any device that drains into the sink or other receptacle must be provided with a check valve or have sufficient air gap in the drainage system as required by the code. The approved air gap is at least double the diameter of the supply pipe measured vertically above the overflow rim of the vessel and in ant case, less than 1 inch. While the devices suggested by the prior art may satisfy these requirements, there is a danger that the plumbing regulations may be difficult to follow when the waste bag is positioned atop of a tilted table, with the plug being positioned too close to the overflow level.

My co-pending application discloses a mounting assembly for a liquid waste line of a medical treatment apparatus that can be mounted on a rim of a sink or other waste receptor, for instance a toilet bowl or a sink. The mounting assembly of that application relies on a suction cup mountable on a rim of the waste receptor, which supports a connector member, one end of which is securable to the discharge nozzle of a medical treatment device, and the other end of which carries a suction cup. While this mounting assembly works satisfactory under most circumstances, subsequent tests showed that a strong discharge current may occasionally displace the orientation of the nozzle and shift the angle of the discharge flow. There exists, therefore, a need to more firmly secure the connector member in a desired orientation in relation to a waste receptor.

The present invention contemplates elimination of drawbacks associated with the prior art and provision of a mounting assembly for a drainage tube that can be mounted directly on the rim of a sink or other waste receptor with sufficient air gap to satisfy the plumbing regulations, while securely retaining the connector in a desired orientation.

SUMMARY OF THE INVENTION

It is, therefore, an object of the present invention to provide a mounting assembly for a liquid waste line of a medical treatment apparatus that can be mounted on a rim of a sink or other waste receptor.

It is another object of the present invention to provide a mounting device that can be easily and efficiently engaged and disengaged from the rim of the waste receptor as required.

It is a further object of the present invention to provide a mounting device for a waste conduit that allows to satisfy the plumbing code requirements while being easy to use by a patient or a caregiver in a home or hospital environment.

It is still a further object of the present invention to provide a mounting assembly, which allows more secure retention of the discharge nozzle in a desire orientation in relation to the waste receptor.

These and other objects of the present invention are achieved through a provision of a mounting assembly that can be detachably secured to the nozzle of a discharge line for supporting the discharge nozzle above an opening of a waste receptor. The mounting assembly has a connector member, one end of which is securable to the discharge nozzle, and the other end—to a suction cup. The suction cup is mounted on a rim of the waste receptor, such as a sink or a toilet bowl. The connector member has sufficient longitudinal dimension to support the discharge nozzle at a predetermined distance above the waste receptor. A clamp engages the discharge nozzle and hooks to the underside of a toilet bowl rim or with an overflow opening in a sink. The easy-to-use and inexpensive mounting assembly of the present invention may be used by a caregiver in a home or hospital setting.

BRIEF DESCRIPTION OF THE DRAWINGS

Reference will now be made to the drawings, wherein like parts are designed by like numerals, and wherein

FIG. 3 is a perspective view of the mounting assembly of the second embodiment of the present invention in use with a drainage conduit mounted on a rim of a toilet bowl.

DETAILED DESCRIPTION OF THE PREFERRED EMBODIMENT

Figure 1:
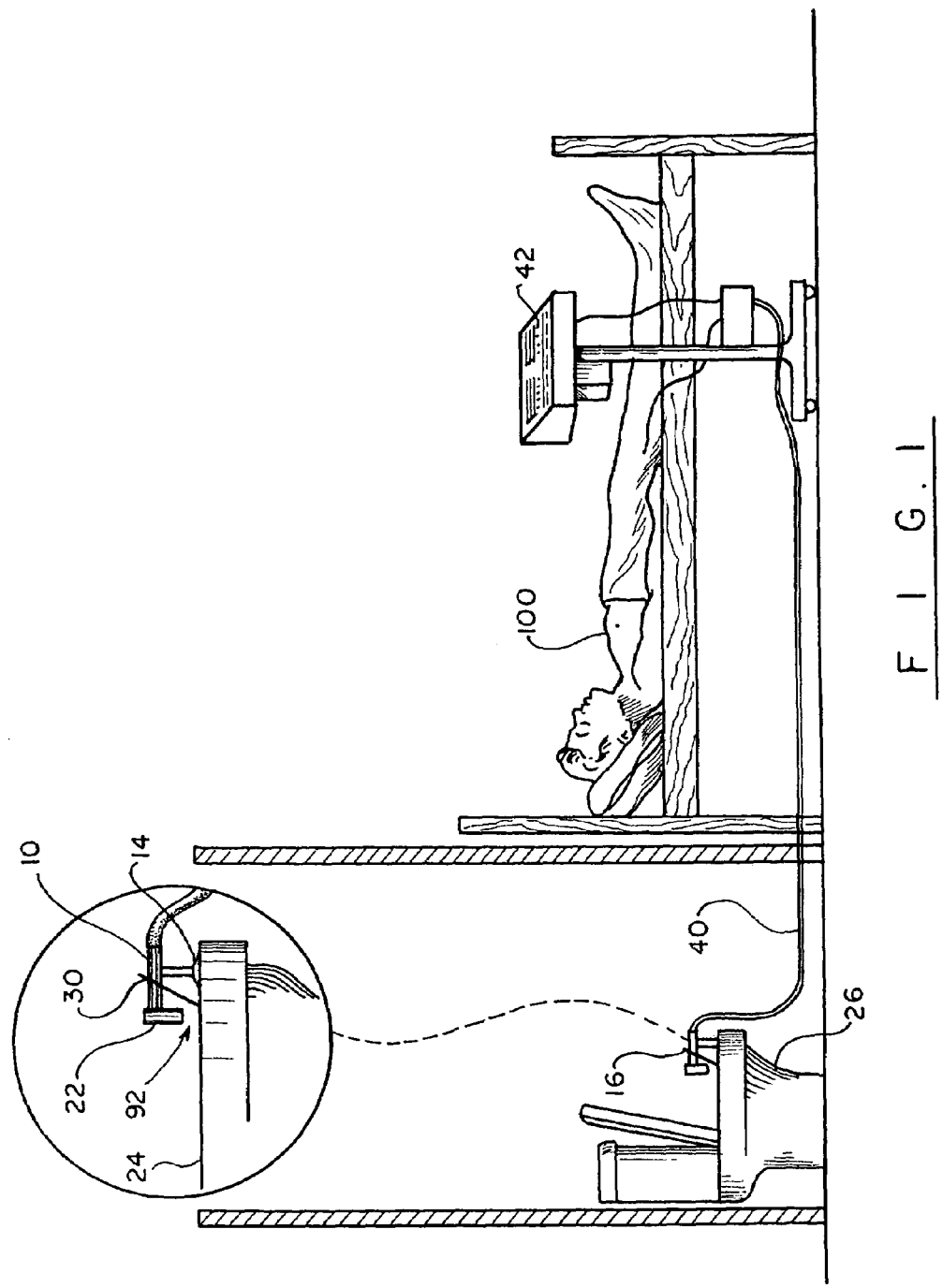
FIG. 1 is a schematic view of the mounting assembly in accordance with the present invention engaged with a nozzle of a drainage line and mounted on a rim of a toilet bowl and connected to a drainage conduit of a medical treatment apparatus.
Figure 2:
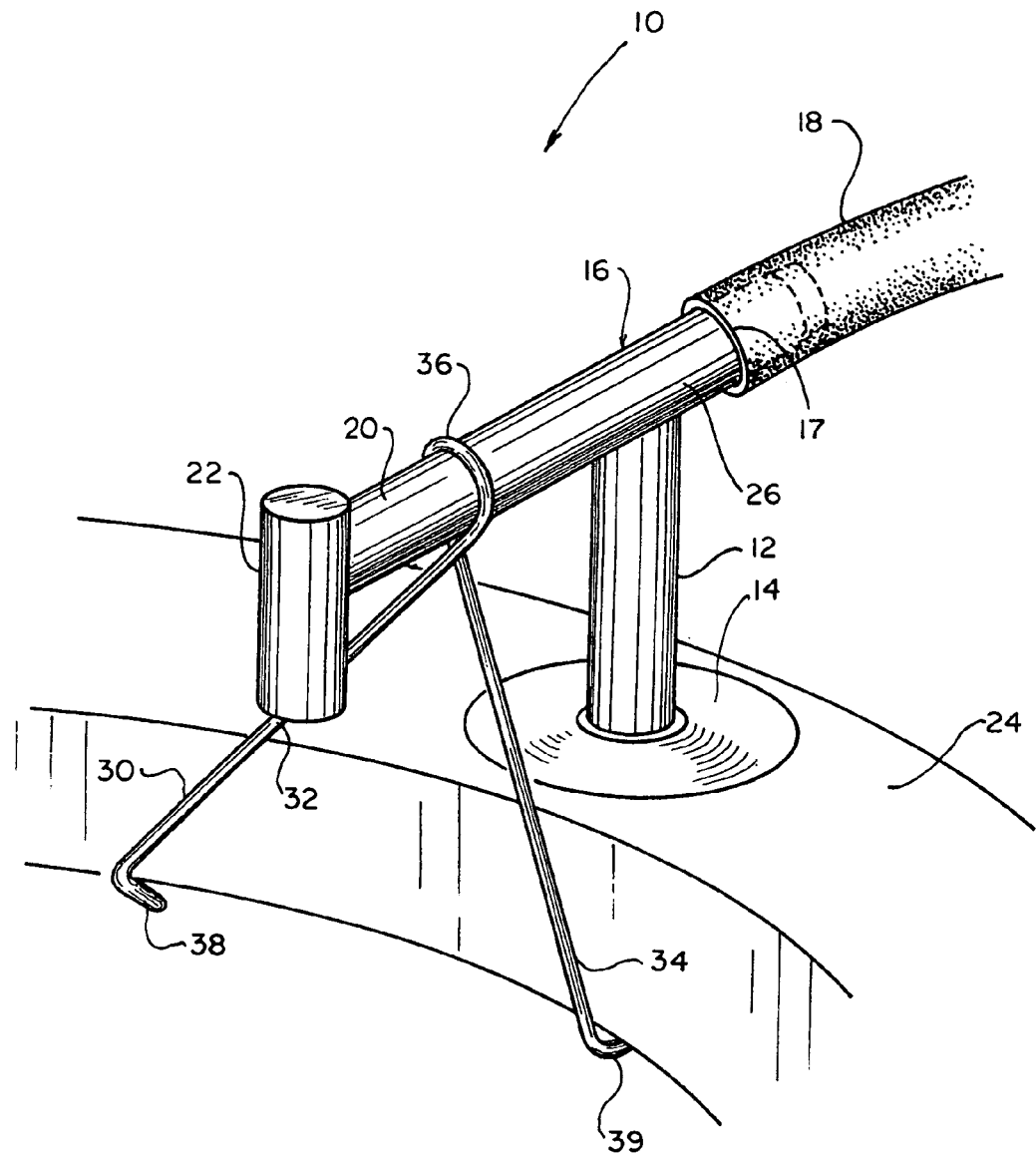
FIG. 2 is a perspective view illustrating the mounting assembly of the first embodiment of the present invention in use with a drainage conduit mounted on a rim of a toilet bowl.

Turning now to the drawings in more detail, numeral 10 designates the mounting assembly in accordance with the first embodiment of the present invention. As can be seen in the drawings, the mounting assembly comprises a connector member 12 and a suction cup 14 detachably engageable with the connector 12. The connector member 12 is formed as an upright support, the lower end of which is engaged with the suction cup 14 and engageable with a discharge nozzle 16 of a waste conduit 18. A free end 20 of the discharge nozzle 16 carries a downwardly oriented spout 22, which has an outlet opening formed in the bottom part thereof.

It should be noted that the nozzle 16 and the spout 22 are of conventional design typically used with a discharge conduit 18 of a medical treatment apparatus 42, such as dialysis machine or other similar devices. The height of the upright connector member 12 is sufficient to support the discharge nozzle 16 at an elevated height above the rim 24 of a toilet bowl 26. The discharge conduit 18 is usually a flexible tube sized to sealingly engage a proximate end 28 of the discharge nozzle 16. During some tests, it was observed that the flexible conduit 18 tends to push against the end 28 and cause the discharge nozzle 16 to somewhat shift its orientation in relation to the open top of the toile bowl 26.

To avoid a possibility of the waste fluid splashing against the rim 24 or missing the open top of the bowl 26, the present invention contemplates provision of a rigid securing clamp 30, which is detachably positioned on the discharge nozzle 16. The clamp 30 has a pair of spaced legs 32, 34 and a central loop portion 36. The loop portion 36 is adapted for wrapping about the discharge nozzle 16. The legs 32, 34 each have a hook-shaped distant end 38, 39, respectively. The ends 38, 39 are configured to engage the underside of the rim of a toilet bowl or other such receptacle and facilitate secure position of the discharge nozzle 16 in relation to the waste receptacle.

FIG. 3 illustrates the second embodiment of the mounting assembly of the present invention. As can be seen in the drawing, the mounting assembly 50 comprises a discharge nozzle 52, which carries a downwardly extending discharge spout 54. A tube connector 56 is unitary connected to the back of the spout 54 and extends in parallel relationship thereto. The opposite end of the discharge nozzle 52 is sealingly engaged with a discharge conduit 58 for establishing a fluid communication between the spout 54 and the medical treatment machine 42. In conventional devices, the tube connector 56 serves as an engagement member for a connecting an attachment device. In the present invention, a supporting connector member 60 is engaged with the tube connector 56, thereby detachably securing the connector member 60 with the discharge nozzle 50.

An opening is formed in a bottom of the tube connector 56 for receiving one end of a supporting connector member 60. The supporting connector member 60 has a first portion 62, a second or middle portion 64, and a third portion 66. The first portion 62 of the connector member 60 is detachably engageable with the tube connector 56 of the spout 56. The second, middle portion 64 of the connector member 60 is unitary engaged with the first portion 62 and extends at 90 or greater degrees in relation to the longitudinal axis of the first portion 62. It is envisioned that the second, middle portion 64 may extend at an obtuse angle in relation to the longitudinal axis of the first portion 62 or at a right angle, depending on the particular requirements.

The third portion 66 of the connector member 60 is bent to form a hook-shaped attachment member that partially encircles a top knob 71 of a suction cup 70. The second part 72 of the suction cup 70 is formed as a dome-shaped body. The longitudinal dimension of the first portion 62 is selected to retain the discharge spout 54 at a sufficient distance above a rim of a waste receptor. In some of the embodiments, the longitudinal dimension of the first portion 62 is at least 0.5" (1.25 cm). In some of the embodiments, the first portion forms an obtuse angle with the second portion 64 so as to retain the discharge spout 54 26 properly oriented above the waste receptor. In the preferred embodiment, the longitudinal dimension of the second portion 64 is at least as great as the radial dimension of the suction cup 14.

Similarly to the first embodiment, a securing clamp 74 is provided for ensuring a proper orientation of the discharge nozzle 52 in relation to the waste receptor. The clamp 74 has a pair of spaced diverging legs 76, 78 and a central loop portion 80. The loop portion is adapted for wrapping about the nozzle 52 behind the tube connector 56. Each of the legs 76, 78 is provided with a hook-shaped end portion, 82, 84, respectively. The hook-shaped ends 82, 84 are adapted to detachably engage the underside of the rim 86 of a waste receptor 90. The clamp 74 facilitates retention of the spout 54 in a desired orientation above the open top of thew waste receptor 90, ensuring that the waste fluid will not miss the waste receptor and the cup 70 does not slip. If desired, the ends of the discharge nozzles 16, 52 are formed with external ridges 17, 53, respectively to ensure a better sealing secure engagement of the conduits 18, 58 with the ends of the nozzles 16, 52.

In operation, when drainage of a dialysate and other waste fluids is required, the user engages the mounting assembly 10 or 50 with the outlet nozzle 16 or 52. The support 12 or the connector member 60 are engaged with suction cups 14, 70. The conduits 18 or 58 are fitted on the ends of the nozzles 16, 52, and the suction cups 14, 70 are mounted on a rim of a waste receptor. A waste discharge line 40 extends from the medical treatment apparatus 42 to a desired location, for instance, adjacent a toilet bowl 26, 90. The rim 24 or 86 of the toilet bowl 26 or 90 serves as a mounting surface for the assembly 10 or 50. A patient 100 may be located some distance from the waste receptor 26, 90.

The waste material with dialysate circulated from the blood stream by the dialysis machine 42 is conducted through the waste conduit 40 into the nozzles 16, 52. The discharge spouts 22, 54 extend above the toilet bowls so that a sufficient air gap 92 (FIG. 1) is formed between the opening in the spout 22, 54 and the surface of water (not shown) in the toilet bowl 26, 90. The caregiver then moves the ends 38, 39 of the clamp 30 or the ends 82, 84 of the clamp 74 to engage the underside of the rim to firmly engage the suction cups 14, 70 and orient the spouts 22, 54 correctly above the toilet bowl 26, 90. The connector members 12 and 60 retain the opening of the discharge spots above the rims 24, 86. The waste fluid is then allowed to discharge through the tubes 18, 58, the nozzles 16, 52 and the spouts 22, 54 directly into the toilet bowl 22, 90 and into the municipal sewerage lines.

The mounting assembly 10 or 50 can be used for positioning the discharge nozzles 16, 52 above a standard sink (not shown). In this case, the suction cups 14, 70 are engaged with the rim of the sink 54 and the legs of the clamps 30, 74 are moved closer together to fit into an overflow opening in the side of the sink.

The connecting member 60 of the mounting assembly 50, as well as the clamps 30, 74 may be formed from bendable non-corrosive material, such as for instance aluminum rods. The suction cups 14, 70 may be formed from a resilient, flexible plastic allowing the suction cups to form the vacuum under the dome and secure the mounting assembly 10, 50 on the toilet bowl or other receptacle. The discharge nozzles 16, 52 may be formed from strong plastic capable of retaining its shape without bending when waste flow passes therethrough.

Many changes and modifications can be made in the design of the present invention without departing from the spirit thereof. I, therefore, pray that my rights to the present invention be limited only by the scope of the appended claims.

I claim:

1. A mounting assembly for a liquid waste discharge line for evacuating waste liquid from a blood treatment apparatus, said liquid waste discharge line comprising a discharge nozzle, said mounting assembly comprising:
   a connector member engageable with the discharge nozzle for supporting the discharge nozzle at a predetermined elevation above a waste receptor;
   a suction cup detachably secured to the connector member, said suction cup being configured for detachable mounting on a rim of the waste receptor; and
   a securing clamp engageable with the discharge nozzle and the rim of the waste receptor for retaining a discharge outlet of the discharge nozzle in a predetermined orientation in relation to the waste receptor.

2. The mounting assembly of claim 1, wherein said securing clamp comprises a rigid body having diverging legs and a loop-shaped central portion, the central portion of the securing clamp being configured to wrap about the discharge nozzle.

3. The mounting assembly of claim 2, wherein each of said diverging legs of the securing clamp comprises a hook-shaped end part configured to detachably engage the rim of the waste receptor below said suction cup.

4. The mounting assembly of claim 1, wherein said connector member is sized and shaped to support the discharge nozzle such that the discharge outlet is oriented above an open top of the waste receptor.

5. The mounting assembly of claim 1, wherein said connector member comprises an upright support engageable with the suction cup and extending upwardly therefrom.

6. The mounting assembly of claim 1, wherein said discharge nozzle comprises an elongated tubular body carrying a tube connector, and wherein said connector member is detachably engageable with the tube connector.

7. The mounting assembly of claim 6, wherein said connector member comprises an elongated rod having a first portion engageable with the tube connector, a second middle portion extending at an angle to the first portion and a third portion engaging the suction cup.

8. A mounting assembly for a liquid waste discharge line for evacuating waste from a medical treatment apparatus, said liquid waste discharge line comprising a flexible tube a proximate end of which is connected to the medical treatment apparatus, said mounting assembly comprising:
   a rigid discharge nozzle adapted for sealing engagement with a distant end of the flexible tube, said discharge nozzle being provided with a discharge spout having a downwardly oriented opening;
   a connector member detachably engageable with the discharge nozzle, said connector member supporting the discharge nozzle such that the opening of the discharge spout extends above an open top of a waste receptor;
   a suction cup detachably secured to connector member, said suction cup being configured for detachable mounting on a rim of the waste receptor; and
   a rigid securing clamp engageable with the discharge nozzle and the rim of the waste receptor for retaining a discharge spout of the discharge nozzle in a predetermined orientation in relation to the waste receptor.

9. The mounting assembly of claim 8, wherein said discharge nozzle is provided with a plurality of ridges formed about an exterior surface of a proximate end of the discharge nozzle to facilitate secure sealing engagement of the discharge nozzle with the flexible tube.

10. The mounting assembly of claim 8, wherein said connector member comprises an upright support engageable with the suction cup and extending upwardly therefrom, an upper end of the connector member supporting the discharge nozzle.

11. The mounting assembly of claim 8, wherein said discharge nozzle comprises an elongated tubular body carrying a tube connector, and wherein said connector member is detachably engageable with the tube connector.

12. The mounting assembly of claim 11, wherein said connector member comprises an elongated rod having a first portion engageable with the tube connector, a second middle portion extending at an angle to the first portion and a third portion engaging the suction cup.

13. The mounting assembly of claim 12, wherein said first portion of the connector member has a longitudinal dimension sufficient to retain the opening of the discharge spout at a pre-determined distance above the waste receptor.

14. The mounting assembly of claim 8, wherein said securing clamp comprises a rigid body having diverging legs and a loop-shaped central portion, the central portion of the securing clamp being configured to wrap about the discharge nozzle.

15. The mounting assembly of claim 14, wherein each of said diverging legs of the securing clamp comprises a hook-shaped end part configured to detachably engage the rim of the waste receptor below said suction cup.

16. A method of supporting a liquid waste discharge line for evacuating waste from a medical treatment apparatus, said liquid waste discharge line comprising a flexible tube having a proximate end connected to the medical treatment apparatus, said method comprising the steps of:

providing a discharge nozzle and connecting the discharge nozzle to a distant end of the flexible tube;

providing a rigid securing clamp and engaging the securing clamp with the discharge nozzle;

providing a connector member and a suction cup attached to the connector member;

securing one end of the connector member to the discharge nozzle;

mounting the suction cup on a rim of a waste receptor such that a discharge opening of the discharge nozzle extends a distance above the waste receptor; and engaging the securing clamp with the waste receptor below the suction cup, thereby supporting the discharge nozzle in a desired orientation on the waste receptor and facilitating evacuation of liquid waste from the medical treatment apparatus directly into the waste receptor.

17. The method of claim 16, further comprising the step of providing the securing clamp with diverging legs and providing a hook-shaped portion on a distant end of each of the legs.

18. The method of claim 17, further comprising the step engaging the hook-shaped portions of the legs with a rim of a waste receptor.

* * * * *